(12) United States Patent
Takabayashi et al.

(10) Patent No.: US 7,570,985 B2
(45) Date of Patent: Aug. 4, 2009

(54) METHOD AND APPARATUS FOR MAGNETIC RESONANCE IMAGING USING CONTRAST AGENT

(75) Inventors: Naoyuki Takabayashi, Tokyo (JP); Yutaka Fukushima, Tokyo (JP)

(73) Assignee: Kabushiki Kaisha Toshiba, Minato-Ku, Tokyo (JP)

( * ) Notice: Subject to any disclaimer, the term of this patent is extended or adjusted under 35 U.S.C. 154(b) by 941 days.

(21) Appl. No.: 10/288,295

(22) Filed: Nov. 6, 2002

(65) Prior Publication Data
US 2003/0158476 A1    Aug. 21, 2003

(30) Foreign Application Priority Data
Feb. 20, 2002   (JP)   ............................. P2002-042577

(51) Int. Cl.
*A61B 5/05*   (2006.01)
(52) U.S. Cl. ................ 600/420; 600/407; 600/410; 600/413; 600/419; 324/307; 324/308; 324/309; 324/310; 324/311
(58) Field of Classification Search ................. 600/407, 600/408, 410–423, 428, 431; 324/318–322, 324/307–311; 424/9.3
See application file for complete search history.

(56) References Cited

U.S. PATENT DOCUMENTS

| | | | |
|---|---|---|---|
| 4,599,565 A | 7/1986 | Hoenninger, III et al. | |
| 5,368,033 A * | 11/1994 | Moshfeghi | 600/419 |
| 5,459,769 A | 10/1995 | Brown | |
| 5,827,187 A * | 10/1998 | Wang et al. | 600/419 |
| 6,167,293 A * | 12/2000 | Chenevert et al. | 600/420 |
| 6,647,283 B2 * | 11/2003 | Klotz | 600/425 |
| 6,741,881 B2 * | 5/2004 | Prince | 600/420 |
| 6,912,415 B2 * | 6/2005 | Kruger et al. | 600/410 |

FOREIGN PATENT DOCUMENTS

| | | |
|---|---|---|
| JP | 62-72327 | 4/1987 |
| JP | 62-216199 | 9/1987 |
| JP | 6-114049 | 4/1994 |

OTHER PUBLICATIONS

98G30898—U.S.A.; Magnetic Resonance Imaging Apparatus; Masashi Ookawa; U.S. Appl. No. 09/644,973, filed Aug. 24, 2000; pp. 1-21 with 5 sheets of drawings.

* cited by examiner

*Primary Examiner*—Brian Casler
*Assistant Examiner*—Baisakhi Roy
(74) *Attorney, Agent, or Firm*—Nixon & Vanderhye PC

(57) ABSTRACT

Monitor scans are performed before imaging scans with respect to a patient injected with a contrast agent. Magnetic resonance images of a plurality of slices of the patient are acquired, usually continuously, in the monitor scans. Projection images are generated from the magnetic resonance images for the plurality of slices, and these projection images are dynamically displayed images. The operator observes the monitor image and issues an instruction for imaging scans. Since a projection image is displayed as the monitor image, then even if a blood vessel is distributed over a three-dimensional area, the operator is still able to ascertain accurately the timing at which the contrast agent reaches the diagnostic region.

28 Claims, 9 Drawing Sheets

METHOD AND APPARATUS FOR MAGNETIC RESONANCE IMAGING USING CONTRAST AGENT

CROSS-REFERENCE TO RELATED APPLICATIONS

This application is based upon and claims the benefit of priority from the prior Japanese Patent Application No. 2002-42577, filed on Feb. 20, 2002; the entire contents of which are incorporated herein by reference.

TECHNICAL FIELD

The present invention relates to a magnetic resonance imaging apparatus and method, and more particularly, to a magnetic resonance imaging apparatus and method wherein a contrast agent is injected into a blood vessel of a patient, magnetic resonance images for observing the flow progress thereof are acquired by means of monitor scans, and magnetic resonance images of an image region of interest are acquired by imaging scans, in response to the arrival of the contrast agent at the image region of interest.

BACKGROUND OF THE INVENTION

In general, a magnetic resonance image obtained by means of a monitor scan is called a 'monitor image' and a magnetic resonance image obtained by means of an imaging scan is called an 'MR image'.

The nuclear spin of a patient's body tissue situated in a static magnetic field generates a magnetic resonance signal ("MR signal") when excited by a radio frequency excitation pulse ("RF pulse") having the corresponding Larmor frequency, and magnetic resonance images of the patient are obtained by means of this MR signal. A large amount of diagnostic information, such as anatomical diagnostic information, and also biochemical information and functional diagnostic information, and the like, can be obtained from these magnetic resonance images, and therefore magnetic resonance imaging apparatuses have become indispensable in the field of present-day medical diagnostic imaging.

A contrast agent is sometimes used in order to capture moving images of blood vessels using a magnetic resonance imaging apparatus of this kind. A contrast agent increases the contrast of the images. According to this method, the contrast agent is injected into the blood vessels of the patient, and when the contrast agent reaches the image region of interest, imaging scans are taken in order to acquire MR images of the image region of interest. In this method, it is important that the acquisition of the MR signal starts at the timing at which the contrast agent enters into the image region of interest. However, since the flow rate of the contrast agent differs according to the patient, it is difficult to obtain this timing.

One method for obtaining this timing is fluoro-triggered-enhanced MRA (Magnetic Resonance Angiography). This is an imaging technique wherein monitor scans are performed after the contrast agent has been injected into the patient's blood vessels. Before taking imaging scans of the image region of interest of the patient, monitor scans are performed in a monitor region, which is a separate region from the image region of interest, situated upstream in the blood flow passing through the blood vessels of the image region of interest. In this monitor scanning, a plurality of images are generated in consecutive fashion and displayed in sequence on a monitor. The operator is able to observe the state of flow of the contrast agent into the monitor region, in real time, by means of the displayed monitor images, and hence he or she can ascertain the timing at which the contrast agent arrives at the diagnostic region.

The images of the monitor region displayed as monitor images may be magnetic resonance images obtained after the contrast agent has been injected, or they may be difference images obtained by subtraction of a magnetic resonance image before contrast agent injection and a magnetic resonance image obtained after the contrast agent has been injected.

Since the monitor images are two-dimensional magnetic resonance images having a prescribed slice thickness, they do not provide satisfactory dynamic imaging of the state of travel in a blood vessel which extends three-dimensionally. On the other hand, if the slice thickness is set to a large thickness of 20 mm to 30 mm in order to include the state of travel in the blood vessel, then equalization of the MR signals in the slice direction occurs, the contrast of the blood vessel declines, and hence the blood vessel becomes difficult to identify.

Therefore, the operator becomes unable clearly to identify the flow of the contrast agent. As a result, problems may arise in that the operator misses the timing at which to instruct performance of imaging scans, and hence the desired MR images cannot be acquired.

BRIEF SUMMARY OF THE INVENTION

The magnetic resonance imaging apparatus and method of the present invention were devised with the foregoing in view, an advantage thereof being to enable monitor images indicating the state of flow of a contrast agent in a patient to be displayed in a beneficial way, thereby facilitating identification of the start timing for imaging scans by the operator.

According to one aspect of the present invention, there is provided a magnetic resonance imaging apparatus comprising: monitor image acquiring means for acquiring magnetic resonance images of a plurality of slices of a monitor region of a patient, on the basis of a pulse sequence for monitor scans; projection means for repeatedly generating projection images by performing projection processing on the magnetic resonance images of the plurality of slices acquired by said monitor image acquiring means; display means for displaying said projection images; input means permitting input of an imaging scan instruction, whilst said projection images are being displayed; and image acquiring means for acquiring magnetic resonance images of an image region of interest of said patient, on the basis of a pulse sequence for imaging scans, in accordance with the instruction input via said input means.

Additional advantages of the invention will be set forth in the description which follows, and in part will be obvious from the description, or may be learned by practice of the invention. The advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
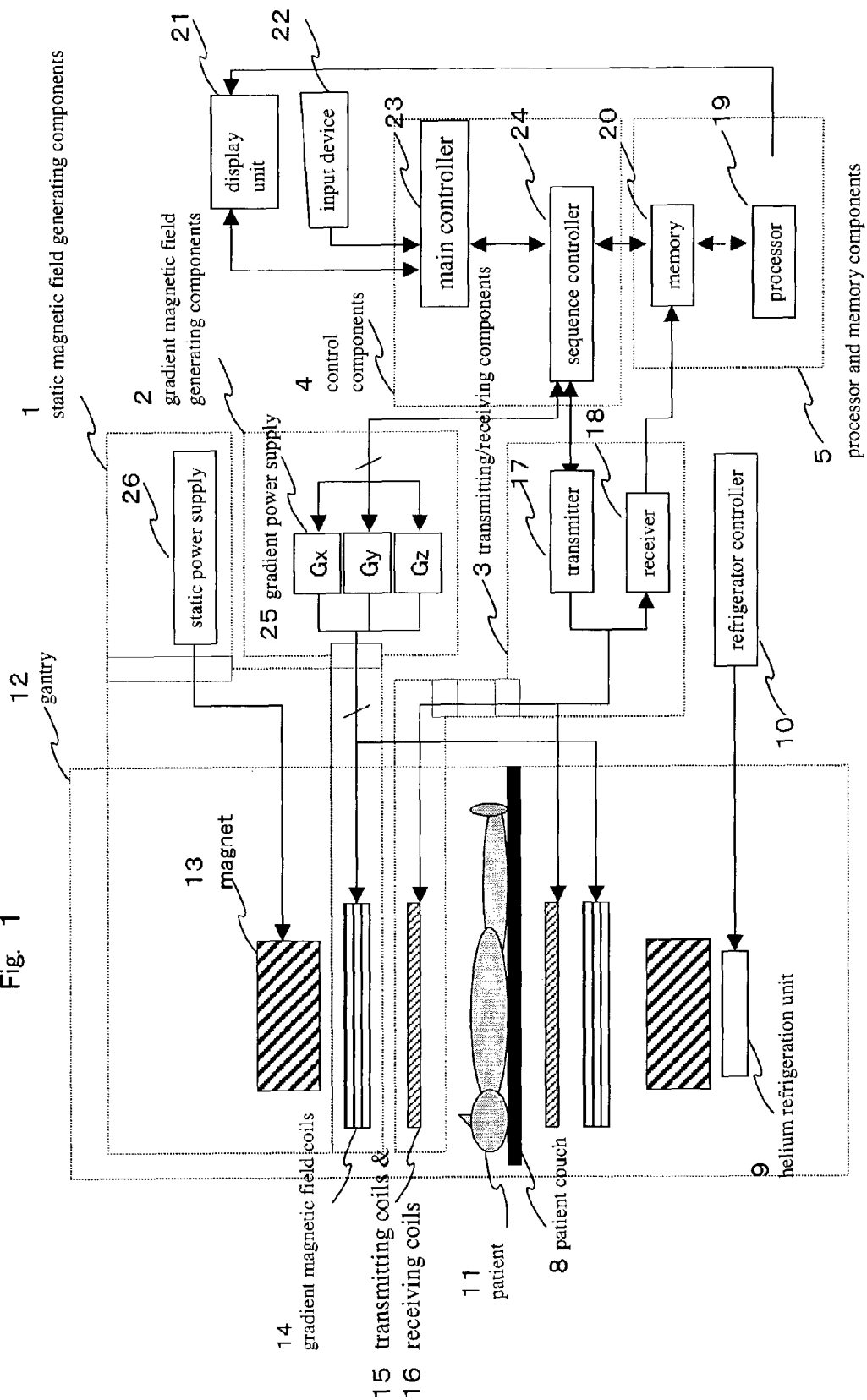
FIG. 1 is a diagram showing the approximate composition of a magnetic resonance imaging apparatus according to a first embodiment of the present invention.

A first embodiment of the present invention is described below. FIG. 1 is a block diagram showing the approximate composition of a magnetic resonance imaging apparatus (MRI apparatus) relating to the first embodiment of the present invention. This apparatus is constituted by static magnetic field generating components 1, gradient magnetic field generating components 2, transmitting/receiving components 3, control components 4, processor and memory components 5, a display unit 21, an input device 22, a patient couch 8, and a gantry 12 into which the patient 11 is inserted.

The static magnetic field generating components 1 comprise a magnet 13, such as a superconducting magnet, for example, and a static power supply 26 for supplying electrical current to the magnet 13, which creates a strong static magnetic field surrounding the patient 11. The static magnetic field generating components 1 are also provided with a helium refrigeration unit 9 and a refrigeration controller 10 for controlling same.

The gradient magnetic field generating components 2 comprise gradient magnetic field coils 14 for generating gradient magnetic fields in mutually orthogonal X, Y and Z axis directions, and a gradient power supply 25 for supplying electrical current to these coils. A gradient signal is supplied to the gradient power supply 25 by a sequence controller 24, for position encoding acquired signals. By controlling the pulse current supplied to the X, Y, Z axis magnetic field coils 14 from the gradient power supply 25 on the basis of this gradient signal, the X, Y and Z axis magnetic fields are synthesized. The mutually orthogonal slice direction gradient magnetic field Gz, phase-encoding direction gradient magnetic field Gx, and frequency-encoding direction (read-out direction) gradient magnetic field can all be set as desired. The gradient magnetic fields in these respective directions are superimposed on the static magnetic field.

The transmitting/receiving components 3 comprise transmitting coils 15 and receiving coils 16 disposed in the vicinity of the patient 11 within the magnet 13, and a transmitter 17 and receiver 18 connected to these coils. The transmitter 17 supplies RF current pulses of a Larmor frequency to the transmitting coils 15. The transmitting coils 15 generate a radio frequency excitation pulse (RF pulse) to excite the nuclei in the patient. The signals radiated by the excited nuclei in the patient 11 are picked up by the receiving coils 16. The receiver 18 reads in the MR signals received by the receiving coils 16 and passes them through various types of signal processing, such as pre-amplification, intermediate-frequency conversion, phase detection, low-frequency amplification, filtering, and the like, whereupon the signals are A/D (analog-to-digital) converted to generate digital data.

The control components 4 comprise a main controller 23 and sequence controller 24. The main controller 23 supplies pulse sequence information to the sequence controller 24, as well as controlling the overall apparatus, by means of installed software (not shown). The sequence controller 24 drives the gradient magnetic field generating components 2, transmitting/receiving components 3, and processor and memory components 5, on the basis of the sequence control information.

In the present embodiment, the monitor scans and imaging scans are performed under the control of the sequence controller 24. In monitor scanning, MR signals are obtained for a plurality of different slices of a monitor region previously set by the operator. The size of the monitor region and the number of slices is set by taking into account the time period for obtaining monitor images. The number of slices is set, for example, to 3, and the slice thickness to 8 mm. In order to display monitor images in real time, a variety of fast imaging methods are used. Furthermore, in order to obtain magnetic resonance images of a plurality of slices in a short timeframe, a multi-slice method using a field-echo method is employed, for example. Any multi-slice method, and not necessarily one based on a field-echo method, may be used, and a variety of pulse sequences may be employed. For a more detailed description of the multi-slice method, reference is made to U.S. Pat. No. 4,599,565 which is incorporated herein by reference. In an imaging scan, MR signals are obtained in the image region of interest previously set by the operator. Imaging scans are not limited to fast imaging methods, and use prescribed pulse sequences.

The processor and memory components 5 comprise a memory 20 and processor 19. The memory 20 stores the digitally converted MR signals from the receiver 18, in a K-space configuration. The processor 19 performs a Fourier transform of the K-space data set and reconstructs a magnetic resonance image in real space. Moreover, the processor 19 is also able to perform subtraction processing or projection processing on the reconstructed magnetic resonance image. In the present embodiment, monitor scanning is performed by acquiring a magnetic resonance image before injection of the contrast agent and a magnetic resonance image after injection of the contrast agent. The magnetic resonance image before injection of the contrast agent is called a "mask image", and the magnetic resonance image after injection of the contrast agent is called a "contrast image". By performing subtraction processing with respect to the mask image and the contrast image, a difference image is obtained. The subtraction processing is carried out once per slice, and a number of difference images corresponding to the number of slices is obtained. A projection image, for example, a MIP image, is derived as a monitor image from the difference images for the plurality of slices thus obtained. A MIP image is described hereinafter.

The display unit 21 displays the monitor images and MR images.

The input device 22 is constituted so as to permit the operator to input parameter information, scan conditions, pulse sequences, information about image processing, and the like, to the control components 4. Moreover, the input device 22 is constituted so as to permit the operator to instruct the start of monitor scanning or imaging scanning.

Figure 2:
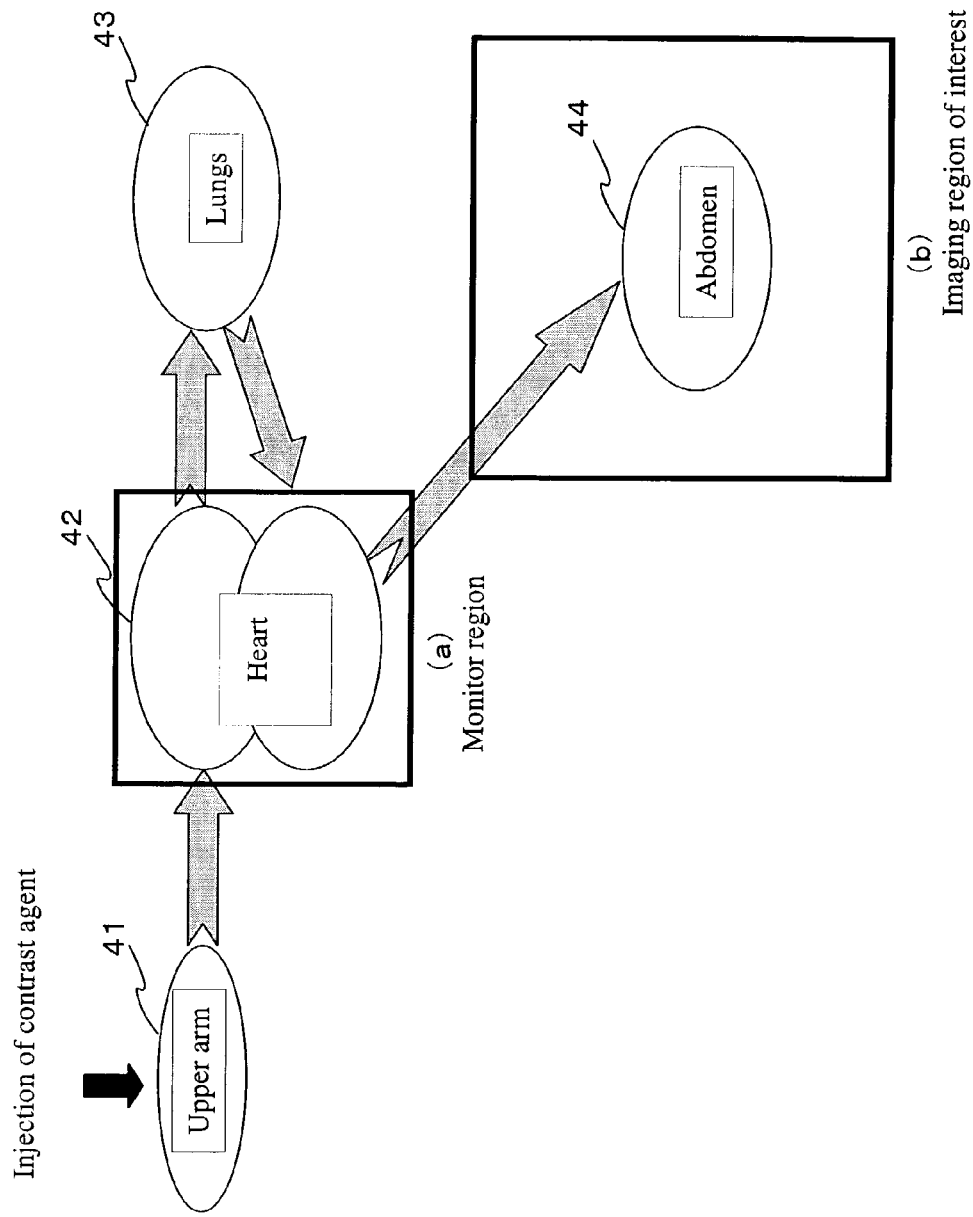
FIG. 2 is a diagram showing the relationship between a monitor region and an image region of interest.

FIG. 2 illustrates a contrast agent injection position, a monitor region and an image region of interest, in a case where the diagnostic region is the abdominal tissue of the patient 11 according to an embodiment of the invention. The monitor region and image region of interest are set to different regions for each patient. A contrast agent injected into a vein of the upper arm 41 passes, together with the venous blood, via the right atrium and right ventricle of the heart 42, into the lungs 43, from whence it is returned with the arterial blood to the left atrium and left ventricle of the heart 42. A portion of the contrast agent leaving the heart 42 arrives at the abdominal tissue in the diagnostic region. The monitor scan is performed in the blood vessel system of the heart 42. The operator sets the heart 42 as the monitor region, confirms the state of flow of the contrast agent therein, and after a prescribed time period, instructs the start of imaging scans via the input device 22. Thereupon, image scans of the abdominal tissue are performed. Here, the prescribed time period indicates the period from the time that the contrast agent leaves the heart 42 until it reaches the tissue of the abdomen 44, and this value is set empirically.

Figure 3:
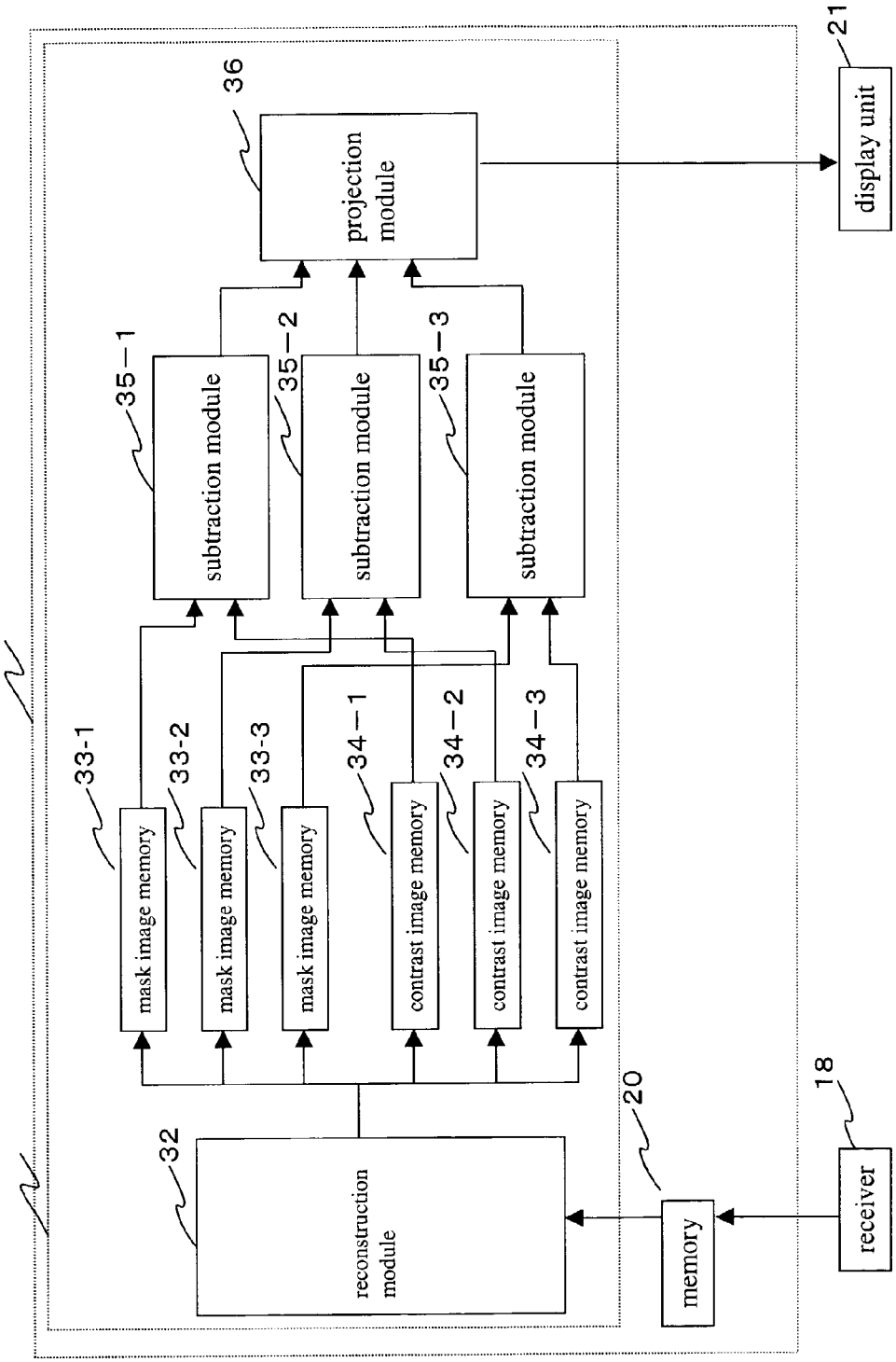
FIG. 3 is a diagram showing the composition of processor and memory components of the first embodiment of the present invention.

FIG. 3 is a detailed block diagram of the processor and memory components 5 according to an embodiment of the invention. The processor and memory components 5 have the functions of performing image reconstruction processing, subtraction processing and projection processing, under the control of the main controller 23. The processor 19 in the processor and memory components 5 comprises a reconstruction module 32, mask image memories 33-1 to 33-3, contrast image memories 34-1 to 34-3, subtraction modules 35-1 to 35-3, and a projection module 36.

Before injecting the contrast agent in the monitor scan, MR signals for three different slices in the monitor region are obtained, and K space data sets corresponding three mask images are recorded in the memory 20.

Thereupon, the respective K space data sets are subjected to a two-dimensional complex Fourier transform in the reconstruction module 32, thereby obtaining three mask images. These are stored directly as complex data in the mask image memories 33-1 to 33-3. For example, three mask images of slice thickness 8 mm are reconstructed and stored respectively in the mask image memories 33-1 to 33-3.

Next, in the stage after injection of contrast agent in the monitor scan, three MR signals corresponding to the same slice positions as the mask images are obtained, and K space data sets corresponding to the three contrast images are recorded in the memory 20. Gd-DTPA (gadolinium diethylenetriamine pentaacetic acid) is widely known as a contrast agent, and by means of this contrast agent, the contrast resolution of the patient's tissue and the image definition of the blood vessels are greatly improved. In an MRI apparatus, images are generally captured using three parameters, namely, proton density, longitudinal relaxation time T1, and transverse relaxation time T2. Use of a contrast agent changes T1 and T2, in particular, and causes the contrast in the tissue to increase.

Of the three respective complex image data stored in the mask image memories 33-1 to 33-3 and contrast image memories 34-1 to 34-3, subtraction processing between the mask image and contrast image corresponding to the same slice position is performed respectively by the subtraction modules 35-1, 35-2 and 35-3.

Subtraction methods include complex subtraction and absolute value subtraction. Complex subtraction involves performing subtraction between a mask image and contrast image by separating into a real part and imaginary part, and then finding the absolute value thereof.

Absolute value subtraction, on the other hand, involves determining absolute value image data for the mask image and contrast image respectively, and then performing subtraction on these absolute value image data.

Complex subtraction has an advantage in that it avoids the loss of signal flow which occurs when a high concentration of contrast agent is injected. Absolute value subtraction, on the other hand, makes it possible to reduce the artifacts if there is movement of the patient 11.

Since each of the subtraction methods has respective advantages and disadvantages in this way, it is possible to devise that either of the methods may be selected, in accordance with the imaging conditions.

By subtraction of the mask image and contrast image, the image data of the patient tissue which is not related to the contrast agent is diminished, and only the image of the contrast agent flowing in the blood vessels is emphasized. In this way, the respective difference images of each slice obtained by the subtraction processing depict only the portion of the blood vessels which the operator intends to observe.

The projection module 36 performs projection image processing on the three adjacent difference images in the slice direction obtained in this way, in order to connect the blood vessels sections thereof. Desirably, MIP processing (Maximum Intensity Projection processing), for example, is used for the projection image processing.

Figure 4:
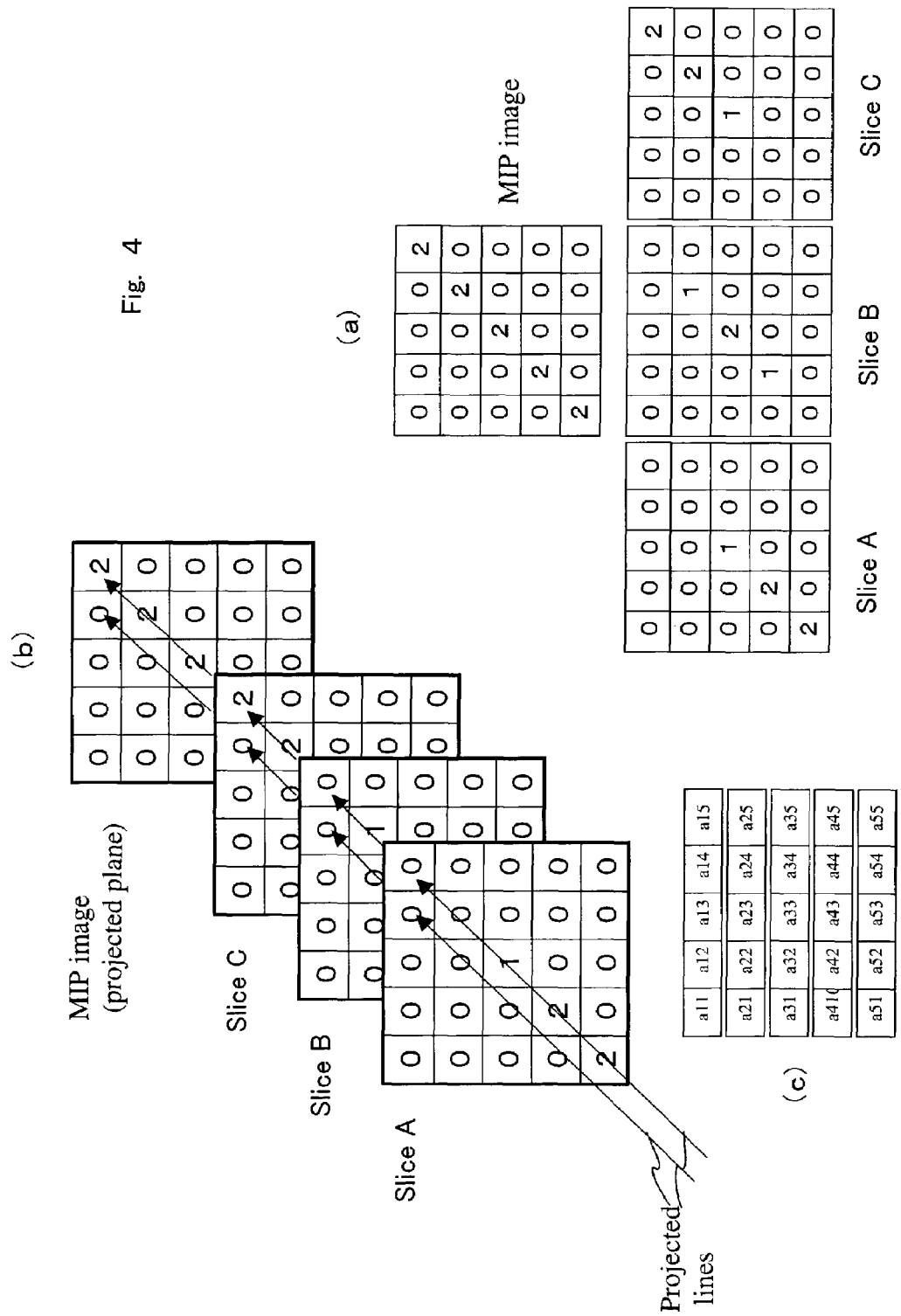
FIG. 4 is a diagram illustrating a method of MIP processing relating to the present invention.

MIP processing takes the maximum value of the pixels of a plurality of image data on the same projected line as the pixel value at the projected place. MIP processing is described in detail with reference to FIG. 4. FIG. 4 shows a schematic representation of three images of different slice positions, each having 5×5 pixels, and one MIP image obtained from these three images according to an embodiment of the invention. In FIG. 4(a), the numerical figures in the respective pixels indicate signal intensity in that pixel.

FIG. 4(b) shows the method for projecting the three images. FIG. 4(c) shows the address of each pixel in the memory. In FIG. 4(b), the projected plane is situated in parallel with the three images (slice A-slice C), and the 25 projected lines linking the centres of the respective pixels (a11-a55) with the centres of the pixels of the MIP image are mutually parallel. Here, focusing on pixel a15, the maximum value of the signal intensities for pixel a15 in slice A to slice C is written as the signal intensity for pixel a15 in the projected plane, in other words, the MIP image. Namely, the signal intensity level 2 for a15 in slice C is taken as the signal intensity of the pixel a15 in the MIP image. An MIP image is obtained by calculating the signal intensities for all of the 5×5 pixels, in a similar manner.

The signal intensity of the contrast agent is markedly greater than the signal intensity of the surrounding body tissue or blood vessels where no contrast agent is present. Therefore, by means of MIP processing, a MIP image which depicts the contrast agent is obtained.

By means of this MIP processing, even supposing that the contrast agent is distributed over a wide range in the slice direction, the state of the contrast agent can still be depicted.

Figure 5:
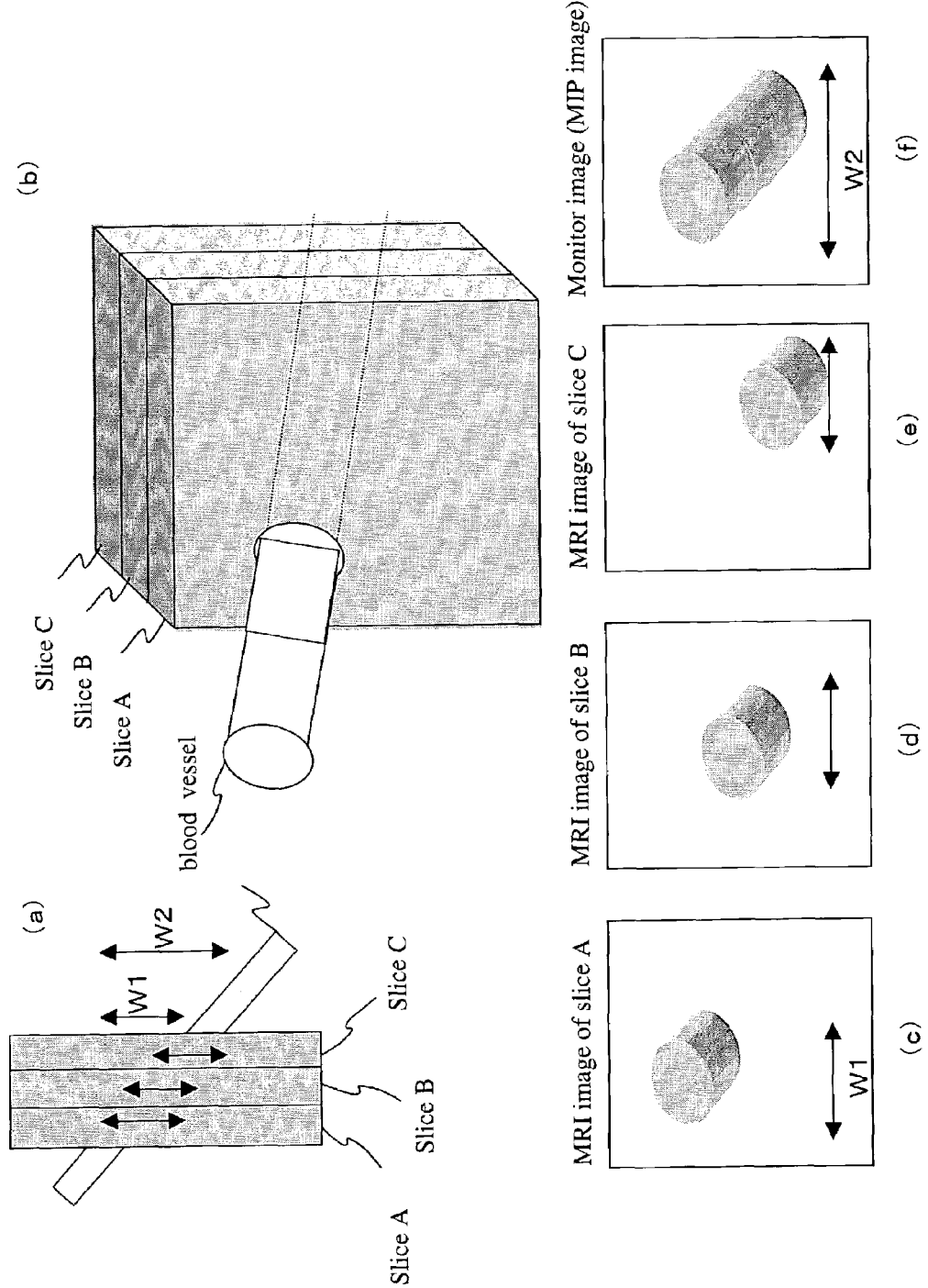
FIG. 5 is a diagram illustrating monitor images which have been MIP processed.

FIG. 5 depicts monitor images obtained by MIP processing according to an embodiment of the invention. FIG. 5(a) and FIG. 5(b) show cases where a blood vessel containing a contrast agent passes obliquely with respect to the slice plane. In these cases, only a small portion of the blood vessel is depicted on any one magnetic resonance image (for example, FIG. 5(c)) However, in the present embodiment, by performing MIP processing of three adjacent magnetic resonance images in the slice direction, such as slice A to slice C (FIG. 5(c)-FIG. 5(e)), these images are converted into a single MIP image as shown in FIG. 5(*f*). The MIP image in FIG. 5(*f*) depicts the continuous structure of the blood vessel.

Since the MIP image is able to depict three-dimensional information relating to the blood vessel, the operator is better able to ascertain the flow of contrast agent into the monitor region, whereupon he or she can instruct the start of imaging scans.

Figure 6:
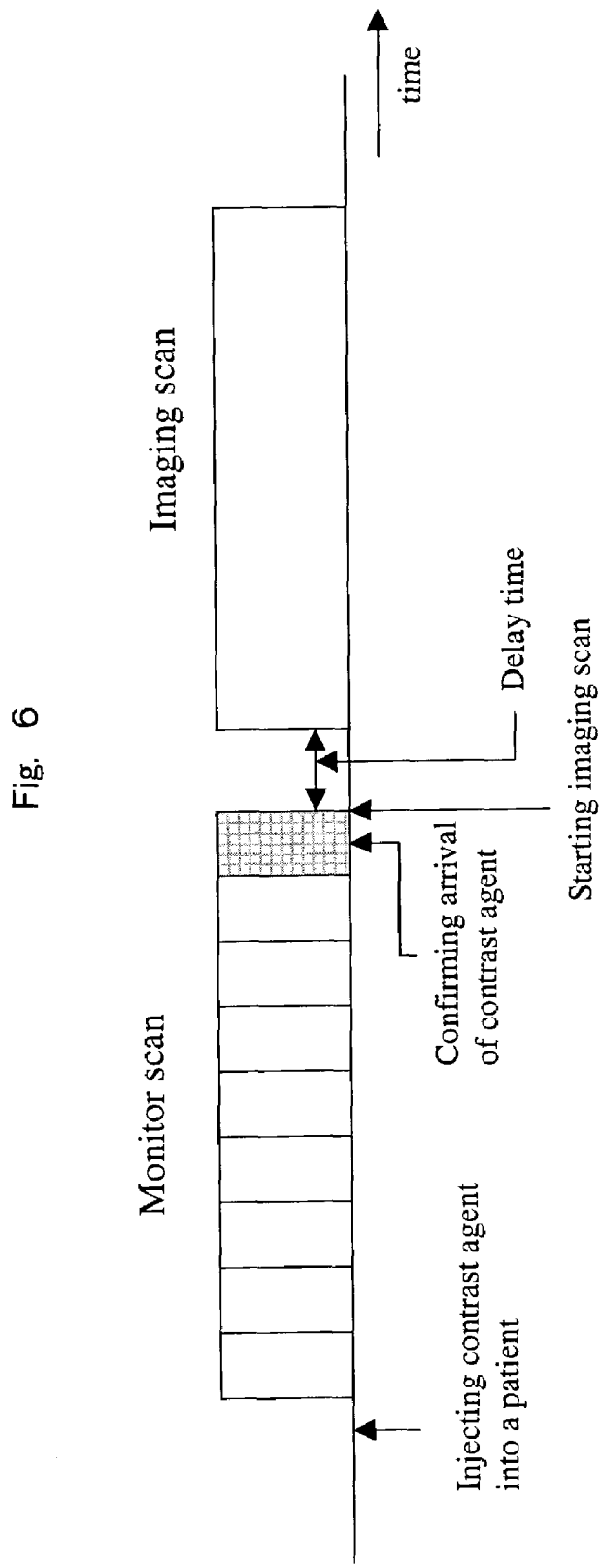
FIG. 6 is a diagram showing the flow of monitor scanning and image scanning.

FIG. 6 shows the flow of monitor scanning and imaging scanning according to an embodiment of the invention. Once the contrast agent has been injected, monitor scanning starts. During monitor scanning, the monitor images are updated successively at a display rate of one frame per second, for instance. When the operator has confirmed that the contrast agent has flowed into a prescribed region of the monitor image, he or she can instruct the start of imaging scans, by means of the input device 22. Moreover, the operator may also set a delay time from the time at which the imaging scan instruction is input until the imaging scan actually starts, taking into consideration the amount of time the contrast agent takes to reach the image region of interest from the monitor region.

As described above, in the monitor scan, since a MIP image is displayed, the operator is able to confirm the timing at which the contrast agent reaches the diagnostic region, with good accuracy, in real time. Therefore, the operator is readily able to ascertain the start timing for the imaging scans. The present invention is especially valuable in cases where the blood vessel is distributed over a large range in the slice direction.

The monitor image is usually displayed in real time. In other words, the time taken to acquire image data, reconstruct an image, and display the image should be as short as possible. Therefore, desirably, the monitor region is set to the minimum required size which permits the progress of the flow of contrast agent to be observed. For example, the time required to acquire three magnetic resonance images each having 64×64 pixels by means of a field-echo method, and to convert and display these images as a MIP image is approximately one second. In the field-echo method, supposing that the repetition time is 5 msec and the phase encoding number is 128, the scan time will be 640 msec. Since the monitor images are obtained by performing image reconstruction processing, projection processing, and the like, on the received signals, the frame rate is approximately one frame per second. In other words, the monitor image is displayed dynamically at approximately one frame per second. In the imaging scans, on the other hand, if obtaining a three-dimensional MR image by acquiring 256×256 pixel images in 28 slices, then the time required from the start of the imaging scans until the MR image is displayed will be approximately 20 seconds, supposing that a three-dimensional fast-field-echo method is used and that the repetition time TR is 3.5 msec, the echo time TE is 1.2 msec, the phase encoding number is 160, and the slice number is 20.

By suitably adjusting the phase encoding number of the pulse sequences for acquiring MR signals or the number of samples per echo, it is possible to change the number of pixels per image, and in the monitor scans according to the present embodiment, the number of pixels is set to a low number, in order to obtain monitor images in a short period of time.

Figure 7:
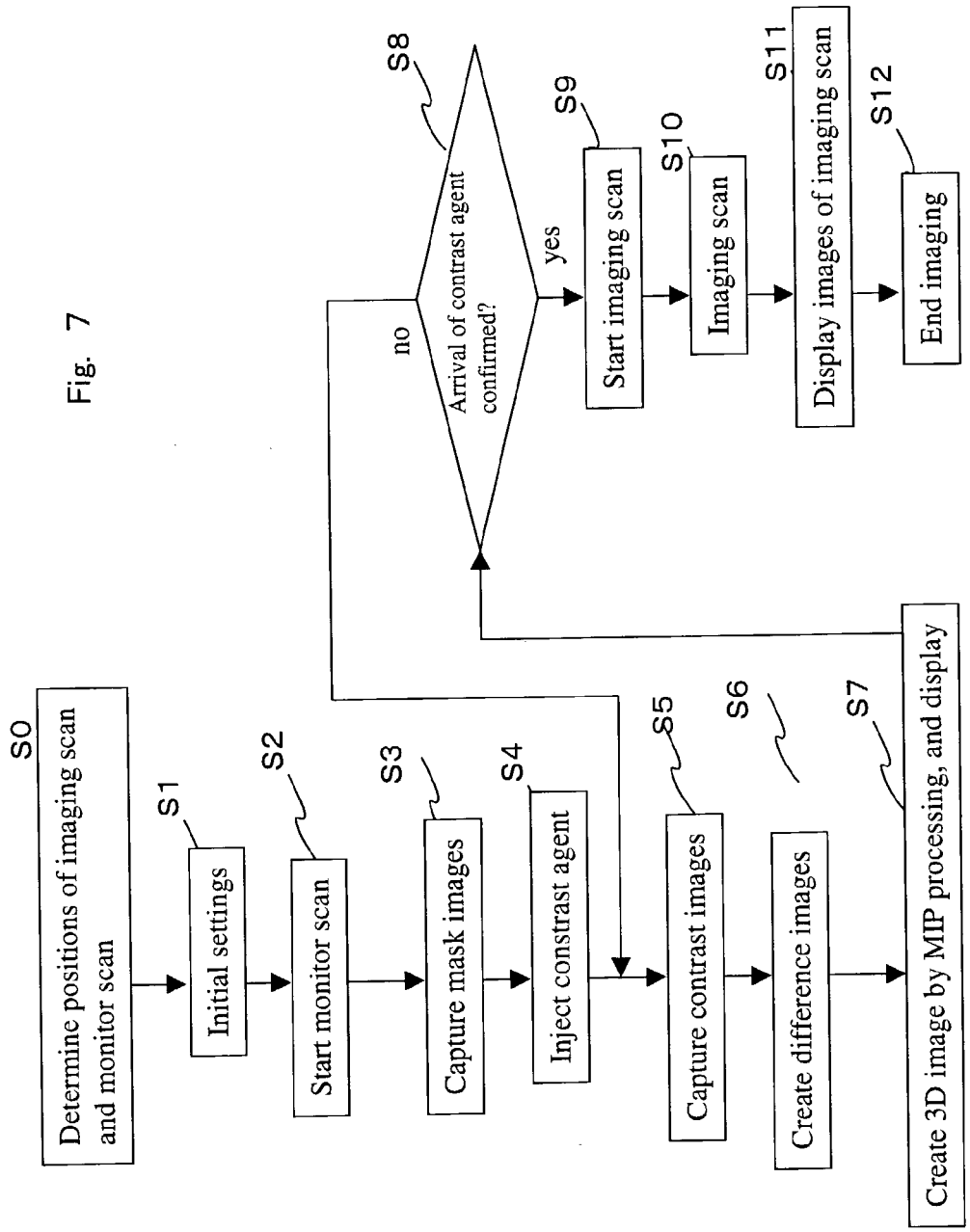
FIG. 7 is a diagram showing an image acquisition procedure flowchart according to the first embodiment of the present invention.

FIG. 7 is a flowchart showing the procedure from monitor scanning to image scanning according to the first embodiment. The position of the image region of interest and monitor region are determined by the operator, and this positional information is recorded in the main controller 23 (step S0), whereupon the initial settings for monitor imaging are made. More specifically, the size and gradation of the display image are determined, the subtraction method is selected, the display screen is selected, and the projection method and pulse sequences are chosen, and so on (step S1).

Thereupon, the operator inputs a monitor scan start instruction via the input device 22, thereby starting monitor scanning. For example, three mask images which are adjacent in the slice direction are reconstructed from the MR signals for three slices obtained by means of a field-echo multi-slice method. Moreover, these three images are recorded directly in the form of complex image data, in the mask image memories 33-1 to 33-3, respectively (step S2-S3).

Next, a contrast agent is injected into a blood vessel of the patient 11 (step S4), and after an appropriate interval time has passed, contrast images are acquired, in a similar fashion to the acquisition of mask images. In other words, three contrast images are acquired at the same locations as the mask images, using the same pulse sequence as that used for acquiring mask images, and these images are stored in the form of complex image data in the contrast image memories 34-1, 34-2, 34-3, respectively (step S5). Moreover, using the three mask images and three contrast images, three difference images are obtained by subtraction of the respective mask image and contrast image for the same position (step S6). Thereupon, one MIP image is generated as a monitor image by performing MIP processing on these three difference images, and the MIP image is displayed on the display unit 21 (step S7).

When the single MIP image has been displayed, the sequence returns to step S5, and the processes of acquiring three contrast images, acquiring three difference images and generating one MIP image are performed again. The MIP image is displayed on the display unit 21. In this way, the operations of step S5 and step S7 are repeated (steps S5 to S7) until, at step S8, an imaging scan start instruction is input by the operator. The MIP image is dynamically displayed virtually in real time, at a rate of one frame per second.

The operator observes the MIP image displayed on the display unit 21, and when he or she confirms that the contrast agent has reached a prescribed position (step S8), he or she inputs an instruction to start imaging scans, via the input device 22. This imaging scan start instruction is transmitted via the main controller 23 to the sequence controller 24, which sets an imaging scan pulse sequence. When the setting preparations have been completed, imaging scans are started and high-resolution MR images are acquired and displayed (steps S9-S11).

It is previously set at step S1 whether the subtraction processing at step S6 will be absolute value subtraction or complex subtraction, but this setting can be changed during the display of the monitor images.

As described above, by MIP processing of the difference images, the contrast agent can be depicted clearly, and therefore the operator is able to ascertain accurately the timing of the start of the imaging scan.

Next, a second embodiment is described, wherein the signal processing is simplified with respect to the first embodiment. In this second embodiment, MIP processing is carried out directly on the contrast images. In general, the contrast agent has a strong contrast in the image, and therefore it is depicted in a emphasized fashion compared body tissue and blood vessels which do not contain contrast agent. Consequently, the contrast images may be MIP processed directly and then displayed. The second embodiment is especially beneficial in cases where artifacts arise in the difference images, due to movement of the patient 11, or in cases where it is sought to further shorten the time required to acquire one frame of the monitor image.

Figure 8:
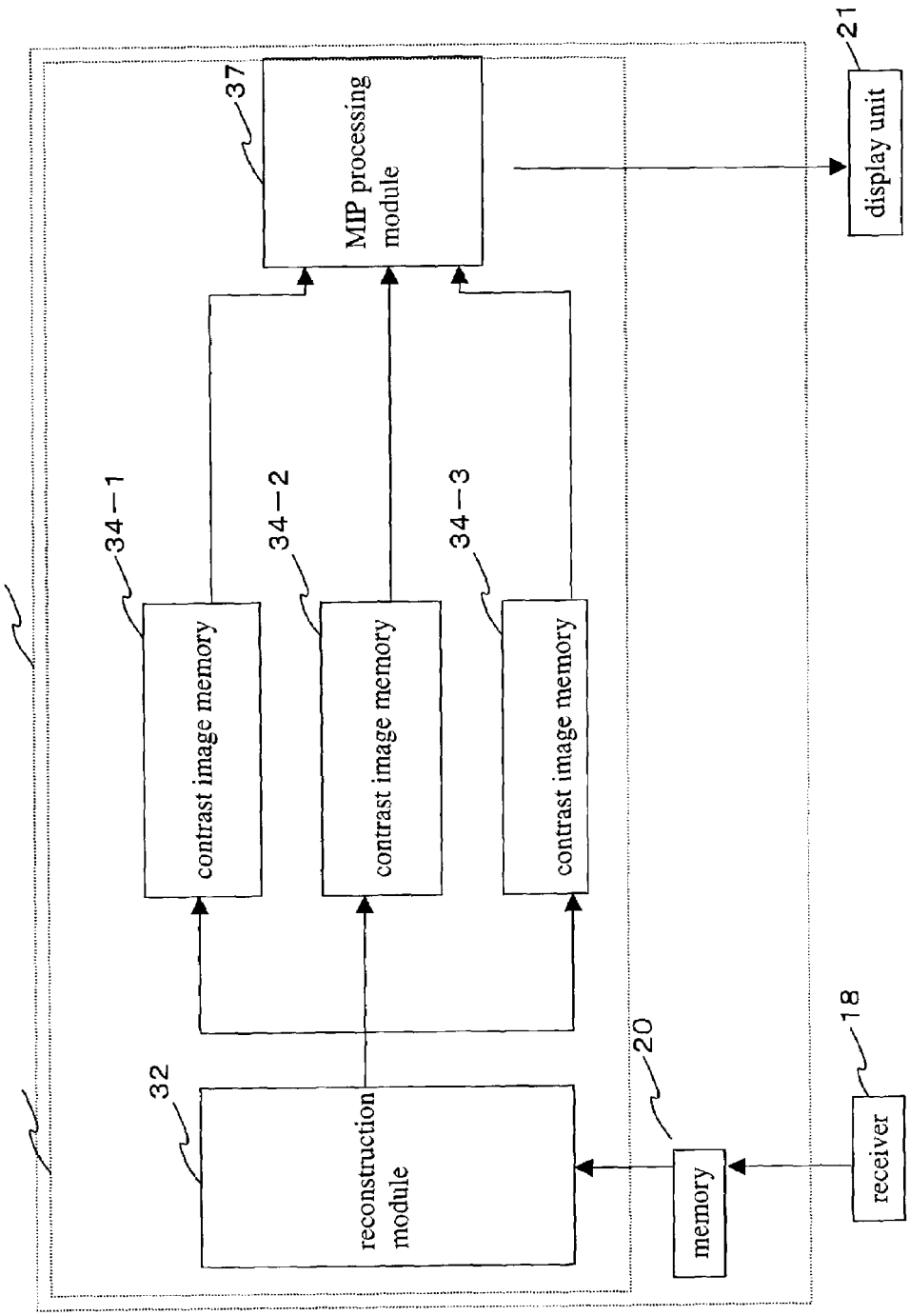
FIG. 8 is a diagram showing the composition of processor and memory components of a second embodiment of the present invention.

FIG. 8 is a detailed block diagram of the processor and memory components 5 according to an embodiment of the invention. The processor 19 in the processor and memory components 5 comprises a reconstruction module 32, contrast image memories A, B, C 34-1 to 34-3, and an MIP processing module 37. The three contrast images stored in the contrast image memories 34-1 to 34-3 are converted directly to an MIP image by the MIP processing module 37.

Figure 9:
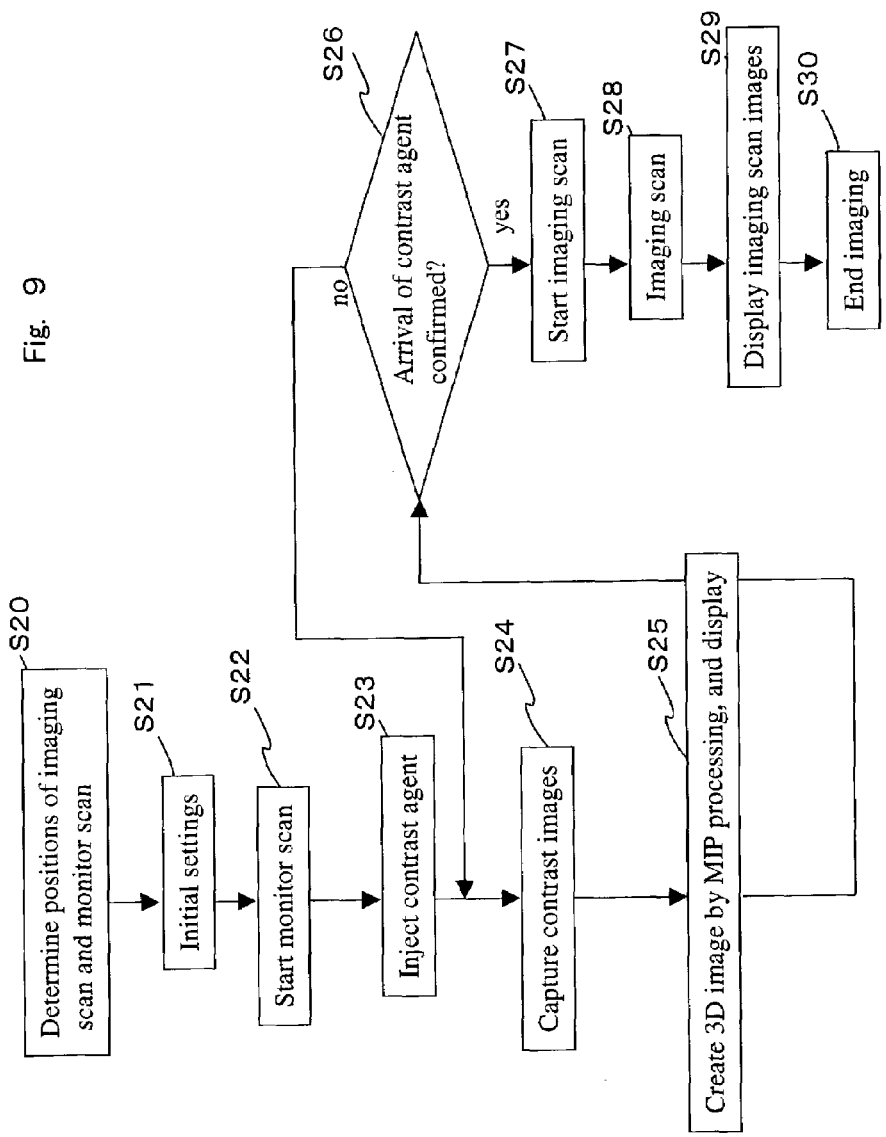
FIG. 9 is a diagram showing an image acquisition procedure flowchart according to the second embodiment of the present invention.

FIG. 9 is a flowchart showing the procedure from monitor scanning to image scanning according to the second embodiment. This second embodiment differs from the first embodiment in that no acquisition of mask images is performed, and no subtraction processing is performed, but in all other respects, it involves the same processing as the first embodiment. When the position of the image region of interest and monitor region has been set by the operator, and this positional information has been stored in the main controller 23 (step S20), the initial settings for monitor imaging are made. More specifically, the size and gradation of the display image is determined, the display screen is selected, and the projection method and pulse sequences are chosen, and the like (step S21). Thereupon, the operator injects a contrast agent into a blood vessel of the patient 11 (step S23), and after an appropriate interval time has passed, contrast images are acquired. In other words, three adjacent contrast images in the slice direction are reconstructed from the MR signals for three slices after injection of the contrast agent, and these three contrast images are stored respectively in the contrast memories 34-1, 34-2, 34-3 (step S24). By performing MIP processing of these three contrast images, a single MIP image is generated, which is displayed on the display unit 21 as a monitor image (step S25). Next, returning to step S24, three contrast images are again acquired and an MIP image is generated therefrom, this MPI image being displayed on the display unit 21. In this way, the operations in step S24 and step S25 are repeated, until the operator issues an imaging scan start signal at step S26. Meanwhile, the operator observes the MIP image displayed in real time on the display unit 21, and when the operator has confirmed that the contrast agent has reached the monitor region (step S26), he or she inputs an instruction to start imaging scans, via the input device 22. Thereupon, imaging scans are performed (steps S27-S29).

Above, specific embodiments of the present invention were described, but the present invention is not limited to the foregoing embodiments and it may be implemented in a modified fashion. For example, MIP processing was described as an image processing method for obtaining a projection image, but it is also possible to use other image processing methods, such as volume rendering, for instance. Despite the relative complexity of the processing it involves, volume rendering has a particular advantage in that it allows blood vessels which are overlapping in the slice direction to be depicted separately. Moreover, in the foregoing description, the number of magnetic resonance images in the monitor scan was taken as three images, but the invention is not limited to this, and any number of two or more images may be used. The number of slices should be set in such a manner that the projection image depicts the three-dimensional extension of the blood vessels and displays same as dynamic images. Furthermore, the position at which imaging scans are performed following the monitor scans in the present invention is not limited to one position only. In particular, when imaging the blood vessels of the thigh, the imaging of the blood vessels is performed successively at a plurality of positions, whilst moving the patient couch 8 in the longitudinal direction of the body, but even in cases such as this, the monitor scanning described in the present invention can be applied prior to performing imaging scans.

As described above, according to the present invention, it is possible to provide a magnetic resonance imaging apparatus whereby the timing at which a contrast agent reaches a diagnostic region can be ascertained accurately by means of monitor scans.

The entire disclosure of Japanese Patent Application No. 2002-42577 filed on Feb. 20, 2002 including specification, claims, drawings and summary are incorporated herein by reference in its entirely.

What is claimed is:

1. A magnetic resonance imaging apparatus comprising:
   monitor image acquiring means for acquiring magnetic resonance images of a plurality of slices of a monitor region of a patient, on the basis of a pulse sequence for monitor scans;
   projection means for repeatedly generating projection images, each projection image being obtained by performing projection processing on the magnetic resonance images of the plurality of slices acquired by said monitor image acquiring means;
   display means for outputting displays of said projection images, said displayed projection images enabling monitor images to indicate the state of flow of a contrast agent in a patient and to facilitate identifying start timing for imaging scans by an operator;
   input means permitting input of an imaging scan instruction while said projection images are being displayed; and
   image acquiring means for acquiring magnetic resonance images of an image region of interest of said patient, on the basis of a pulse sequence for imaging scans, in accordance with the instruction input via said input means wherein the monitor region is situated upstream of the image region with respect to an injected contrast agent.

2. The apparatus according to claim 1, wherein said projection processing is either MIP processing or volume rendering.

3. The apparatus according to claim 2, wherein said projection processing is performed using a projected plane that is virtually parallel to the magnetic resonance images of said plurality of slices.

4. The apparatus according to claim 2, wherein said projection processing is performed using projected lines which are virtually parallel with respect to each other.

5. The apparatus according to claim 1, wherein said plurality of slices are 3 slices.

6. The apparatus according to claim 1, wherein said pulse sequence for monitor scans is a multi-slice method.

7. The apparatus according to claim 1, wherein the magnetic resonance images acquired by means of said pulse sequence for imaging scans have higher resolution than the magnetic resonance images acquired by means of said pulse sequence for monitor scans.

8. The apparatus according to claim 1, wherein said monitor region includes the heart of the patient and said image region of interest includes the abdomen of the patient.

9. A magnetic resonance imaging device comprising:
   a magnet for generating a static magnetic field in which the patient is situated;
   transmitting and receiving coils for transmitting high-frequency magnetic fields onto said patient and picking up magnetic resonance signals from the patient;

a transmitter for transmitting a high-frequency magnetic field based on a pulse sequence onto said patient by means of said transmitting and receiving coils;

a gradient magnetic field power supply for applying a gradient magnetic field based on a pulse sequence to said patient by means of said transmitting and receiving coils;

a receiver for receiving said magnetic resonance signals generated in accordance with the execution of said pulse sequence;

a processing unit for reconstructing magnetic resonance images on the basis of the magnetic resonance signals received by said receiver;

a display unit for displaying the magnetic resonance images reconstructed by said processing unit;

a controller for controlling the operations of said transmitter, receiver and gradient magnetic field power supply, on the basis of said pulse sequence; and an input device permitting input of an instruction for the execution of said pulse sequence to said controller;

wherein said controller executes a monitor scan pulse sequence for a monitor region of said patient in order to observe the flow of contrast agent injected into said patient and, in response to an instruction input via said input means, halts the execution of said monitor scan pulse sequence and executes an imaging scan pulse sequence for an image region of interest of said patient wherein the monitor region is situated upstream of the image region with respect to an injected contrast agent;

said monitor scans involving the acquisition of magnetic resonance images for a plurality of slices of said patient; and said processor unit repeatedly generating and outputting a display of projection images, each projection image being obtained by carrying out projection processing of the magnetic resonance images of the plurality of slices acquired by said monitor scans, said displayed projection images enabling monitor images to indicate the state of flow of a contrast agent in a patient and to facilitate identifying start timing for imaging scans by an operator.

10. The apparatus according to claim 9, wherein said projection processing is either MIP processing or volume rendering.

11. The apparatus according to claim 10, wherein said projection processing is performed using a projected plane that is virtually parallel to the magnetic resonance images of said plurality of slices.

12. The apparatus according to claim 10, wherein said projection processing is performed using projected lines which are virtually parallel with respect to each other.

13. The apparatus according to claim 9, wherein said plurality of slices are 3 slices.

14. The apparatus according to claim 9, wherein said monitor scan pulse sequence is a multi-slice method.

15. The apparatus according to claim 9, wherein the magnetic resonance images acquired by means of said imaging scan pulse sequence have higher resolution than the magnetic resonance images acquired by means of said monitor scan pulse sequence.

16. The apparatus according to claim 9, wherein said monitor region includes the heart of the patient and said image region of interest includes the abdomen of the patient.

17. The apparatus according to claim 9, wherein said monitor scans involve continuously acquiring magnetic resonance images for the plurality of slices of said patient before injection of the contrast agent as mask images, and magnetic resonance images of each the same slice positions as said mask images after injection of the contrast agent, as contrast images;

said processor unit generating difference images for each slice from said mask images and said contrast images for the same slice position, and carrying out projection processing on said plurality of difference images.

18. The apparatus according to claim 17, wherein said projection processing is either MIP processing or volume rendering.

19. A method for displaying images of a monitor region, by acquiring first magnetic resonance images from a monitor region of a patient before acquiring second magnetic resonance images of an image region of interest of a patient situated inside a magnetic resonance imaging apparatus, wherein the monitor region is situated upstream of the image region with respect to an injected contrast agent the method comprising:

acquiring the first magnetic resonance images of a plurality of slices by performing monitor scans of a monitor region of said patient injected with contrast agent;

carrying out projection processing of the first magnetic resonance images of said plurality of slices to obtain a projection image, and repeatedly generating projection images;

dynamically displaying said projection images; and acquiring the second magnetic resonance images by performing imaging scans of said patient in response to an instruction input externally while said projection images are being dynamically displayed, thereby enabling monitor images to indicate the state of flow of a contrast agent in a patient and to facilitate identifying start timing for imaging scans by an operator.

20. A method for displaying images of a monitor region, by acquiring magnetic resonance images from a monitor region of a patient before acquiring magnetic resonance images of an image region of interest of a patient situated inside a magnetic resonance imaging apparatus, the steps comprising:

acquiring magnetic resonance images of a plurality of slices of the monitor region of said patient by means of a pulse sequence for monitor scans, before injection of a contrast agent, as mask images;

acquiring magnetic resonance images of the same slice positions as said mask images by means of a pulse sequence for monitor scans, after injection of the contrast agent, as contrast images;

generating difference images for each slice from said mask image and said contrast image for the same slice position;

carrying out projection processing on said plurality of difference images to generate a projection image and repeatedly generating such projection images;

displaying said projection images as dynamic images; and acquiring magnetic resonance images of an image region of interest of said patient by means of a pulse sequence for imaging scans, in response to an instruction input externally while said projection images are being displayed wherein the monitor region is situated of the image region with respect to an injected contrast agent, said displayed projection images enabling monitor images to indicate the state of flow of a contrast agent in a patient and to facilitate identifying start timing for imaging scans by an operator.

21. A method for magnetic resonance imaging, said method comprising:
repeatedly acquiring magnetic resonance images of a plurality of slices of a monitor region of a patient, on the basis of a pulse sequence for monitor scans;
generating a sequence of projection images of said plurality of slices by performing projection processing on said repeatedly acquired images of plural slices;
displaying said sequence of projection images;
inputting an imaging scan instruction based on observation of said sequence of projection images as they are displayed; and
acquiring magnetic resonance images of an image region of said patient on the basis of a pulse sequence for imaging scans, at a time based on the occurrence of said inputted instruction wherein the monitor region is situated upstream of the image region with respect to an injected contrast agent, said displayed projection images enabling monitor images to indicate the state of flow of a contrast agent in a patient and to facilitate identifying start timing for imaging scans by an operator.

22. A method as in claim 21 wherein said monitor region includes the heart of the patient and said image region includes the abdomen of the patient.

23. A method for magnetic resonance imaging device, said method comprising:
generating a static magnetic field in which a patient is situated;
transmitting high-frequency magnetic fields onto said patient and receiving magnetic resonance signals from the patient;
transmitting a high-frequency magnetic field based on a pulse sequence onto said patient;
applying a gradient magnetic field based on said pulse sequence to said patient;
receiving said magnetic resonance signals generated in accordance with the execution of said pulse sequence;
reconstructing magnetic resonance images on the basis of the received magnetic resonance signals;
displaying said reconstructed magnetic resonance images; and
inputting an instruction for execution of an imaging pulse sequence based on observation of displayed reconstructed monitor images;
wherein a monitor scan pulse sequence is executed for a monitor region of said patient to generate and display monitor region images and observe a flow of contrast agent injected into said patient and, in response to said inputted instruction, halting the execution of said monitor scan pulse sequence and instead executing an imaging scan pulse sequence for an image region of said patient wherein the monitor region is situated upstream of the image region with respect to an injected contrast agent;
said monitor scans including the acquisition of magnetic resonance images for a plurality of slices of said patient and repeatedly generating projection images by carrying out projection processing of magnetic resonance images of the plurality of slices acquired by said monitor scans, said displayed projection images enabling monitor images to indicate the state of flow of a contrast agent in a patient and to facilitate identifying start timing for imaging scans by an operator.

24. A method as in claim 23 wherein said monitor region includes the heart of the patient and said image region of interest includes the abdomen of the patient.

25. A method as in claim 23 wherein said monitor scans:
continuously acquire (a) magnetic resonance images for the plurality of slices of said patient before injection of the contrast agent for use as mask images, and (b) magnetic resonance images of each the same slice positions as said mask images after injection of the contrast agent for use as contrast images;
generate difference images for each slice from said mask images and said contrast images for the same slice position, and
carry out projection processing on said plurality of difference images.

26. A magnetic resonance imaging apparatus comprising:
a reconstruction unit configured to reconstruct magnetic resonance images of a plurality of slices of a monitor region of a patient using a pulse sequence for monitor scans;
a projection unit configured to repeatedly generate projection images, each projection image being obtained by performing projection processing on the magnetic resonance images of the plurality of slices acquired by said reconstruction unit;
a display unit configured to display said projection images; and
an input unit configures to accept input of an imaging scan instruction, while said projection images are being displayed, to thereafter acquire magnetic resonance images of an image region of interest of said patient using a pulse sequence for imaging scans wherein the monitor region is situated upstream of the image region with respect to an injected contrast agent, said displayed projection images enabling monitor images to indicate the state of flow of a contrast agent in a patient and to facilitate identifying start timing for imaging scans by an operator.

27. A method for magnetic resonance imaging, said method comprising:
(i) performing a monitoring operation after injection of contrast agent into a patient which includes:
(a) acquiring MR signals of a monitor region of the patient, on the basis of a pulse sequence for monitor scan;
(b) generating slices at different locations based on the MR signals; and
(c) repeating steps a) through b) until an indication that an image scan of a image region of the patient should begin is received, wherein the monitor region is situated upstream of the image region, said displayed projection images enabling monitor images to indicate the state of flow of a contrast agent in a patient and to facilitate identifying start timing for imaging scans by an operator; and
(ii) performing the image scan and reconstructing magnetic resonance images of the image region.

28. A method for magnetic resonance imaging, said method comprising:
(i) performing a monitoring operation after injection of contrast agent into a patient which includes:
(a) acquiring MR signals of a monitor region of the patient, on the basis of a pulse sequence for monitor scan;
(b) generating monitor images at different locations based on the MR signals; and
(c) repeating steps a) through b) until an indication that an image scan of a image region of the patient should begin is received, wherein the field of view (FOV) of monitor images is smaller than the FOV of the image region, said displayed projection images enabling monitor images to indicate the state of flow of a contrast agent in a patient and to facilitate identifying start timing for imaging scans by an operator; and (ii) performing the image scan and reconstructing magnetic resonance images of the image region.

* * * * *